(12) United States Patent
Orgel et al.

(10) Patent No.: US 6,455,495 B1
(45) Date of Patent: Sep. 24, 2002

(54) METHODS AND COMPOSITIONS FOR DELIVERY OF THERAPEUTIC AGENTS TO BONE TISSUE EMPLOYING CONJUGATES OF NEGATIVELY CHARGED PEPTIDE OLIGOMERS WITH THERAPEUTIC AGENTS

(75) Inventors: Leslie Orgel, La Jolla, CA (US); Barbara Chen Fei Chu, Del Mar, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/367,516

(22) PCT Filed: Feb. 13, 1998

(86) PCT No.: PCT/US98/02811

§ 371 (c)(1), (2), (4) Date: Dec. 14, 1999

(87) PCT Pub. No.: WO98/35703

PCT Pub. Date: Aug. 20, 1998

Related U.S. Application Data

(60) Provisional application No. 60/039,739, filed on Feb. 14, 1997, and provisional application No. 60/050,397, filed on Jun. 20, 1997.

(51) Int. Cl.$^7$ ................................................ A01N 37/18
(52) U.S. Cl. ............................ 514/2; 514/44; 530/350; 435/6; 435/91.2; 435/69.1; 435/325; 435/374; 435/378; 424/422; 424/49; 424/536; 424/23.5; 424/24.32; 424/24.33; 424/24.5
(58) Field of Search ............................ 530/350; 435/6, 435/91.2, 69.1, 325, 374, 378; 514/2, 44; 536/23.5, 24.32, 24.33, 24.5; 424/422, 49

(56) References Cited

FOREIGN PATENT DOCUMENTS

WO    WO 92/20371    * 11/1992

* cited by examiner

*Primary Examiner*—Christopher S. F. Low
*Assistant Examiner*—Hope A. Robinson
(74) *Attorney, Agent, or Firm*—Stephen E. Reiter; Foley & Lardner

(57) ABSTRACT

The invention provides conjugates of negatively charged peptide oligomers with therapeutic agents, moieties capable of recruiting endogenous bone-affecting agents, or imaging agents, useful for delivering the agents to bone tissue or calcified masses, and the methods of use thereof. The negatively charged peptide oligomers bind strongly but reversibly to bone tissue and calcified masses with a controllable affinity and retention time on the tissue or mass.

29 Claims, No Drawings

METHODS AND COMPOSITIONS FOR DELIVERY OF THERAPEUTIC AGENTS TO BONE TISSUE EMPLOYING CONJUGATES OF NEGATIVELY CHARGED PEPTIDE OLIGOMERS WITH THERAPEUTIC AGENTS

This application is a 371 of PCT/US98/02811, filed Feb. 13, 1998 and claims benefit to U.S. Provisional Application Nos: 60/039,739, filed Feb. 14, 1997; and 60/050,397, filed Jun. 20, 1997.

BACKGROUND OF THE INVENTION

Whole bone, which comprises bone tissue, soft tissue, blood vessels and nerves, functions as both a skeletal unit and a physiological unit. Bone tissue is formed of bone cells in an extracellular collagenous matrix. The matrix contains collagen and an inorganic mineral phase called apatite or hydroxyapatite consisting primarily of calcium phosphate crystals. Hydroxyapatite helps provide the necessary stiffness of bone.

Hydroxyapatite has been found to bind tightly to proteins, with calcium sites on the hydroxyapatite appearing to bind acidic groups, e.g., carboxy and phosphate groups, and phosphate sites appearing to bind basic groups. A separation technique known as hydroxyapatite chromatography is based on the interaction of hydroxyapatite with proteins. A variety of hydroxyapatite binding proteins are known to be present in mammalian mineral tissue. These proteins have two known types of binding sites, i.e., one site is believed to be composed of phosphorylated amino acids and the other site is believed to be composed of γ-carboxy glutamic acid. A third type of hydroxyapatite binding site has been hypothesized to consist of consecutive sequences of acidic amino acids. Aspartic acid hexamer ($Asp_6$) and glutamic acid hexamer ($Glu_6$) were shown to significantly adsorb onto hydroxyapatite, with the adsorption of polyglutamic acid decreasing with a reduction in the number of Glu sequences (R. Fujisawa, et al., *Biochimica et Biophysica Acta.*, 1292:53–60 (1996)). $Glu_6$ and conjugates of $Glu_6$ with bovine serum albumin and hemoglobin have been shown to affect the mineralization of hydroxyapatite in the presence of calcium and phosphate (Id.).

Compounds which target and securely bind to bone are of interest for the diagnosis and treatment of diseases of bone. Bone targeting compounds are well known, and include tetracyclines and fluoride. One group of bone targeting compounds, bisphosphonates, have been conjugated with radionuclides and used in skeletal scintillography for the imaging of bone metastases. Bisphosphonates used for bone scanning include hydroxyethylidene diphosphonate, methylene diphosphonate (MDP), hydroxymethylene diphosphonate, and dicarboxypropane diphosphonate, with MDP being the most widely used agent. Additionally, conjugates of bisphosphonates with the antitumor agent methotrexate were found to behave like bone targeting agents with methotrexate being available to treat osteosarcoma (F. Hosain, *J. Nucl. Med.*, 37:105–107 (1996)).

In addition to targeting bone, bisphosphonates function by inhibiting bone resorption through their effect on both osteoblasts and osteoclasts, the bone cells responsible for bone growth and bone resorption, respectively. While the mechanism of action of bisphosphonates on bone is not completely understood, it is clear that it is not entirely a matter of adsorption. Moreover. when given in high doses such as those used to prevent ectopic calcification or ossification, bisphosphonates inhibit the mineralization of normal calcified tissues, which results in rickets and osteomalacia. Renal failure can occur due to formation of insoluble aggregates in blood following rapid intravenous injection of large doses of bisphosphonates. Additionally, a strong bond is formed between bisphosphonates and hydroxyapatite, and it has been suggested that, as bisphosphonates slow the resorption of the bone on which they are deposited, their skeletal retention may approach an entire lifetime. Such a long retention time is disadvantageous in applications where a more controlled and transient bond is required.

It would be a significant advantage to have available methodology and compositions for delivering therapeutic agents and imaging agents to bone tissue, wherein the affinity and retention time on the bone can be easily controlled and varied. The present invention meets these and other needs.

SUMMARY OF THE INVENTION

One aspect of this invention provides methods and compositions for delivery of therapeutic agents to bone tissue employing conjugates of negatively charged peptide oligomers.

Another aspect of this invention provides methods and compositions for recruiting endogenous bone affecting agents present in a subject's body fluid to a subject's bone tissue, employing negatively charged peptide oligomers conjugated with moieties capable of binding the endogenous bone affecting agents.

Another aspect of the invention provides methods and compositions for imaging bone tissue or calcified masses employing conjugates of negatively charged peptide oligomers with imaging agents.

A further aspect of this invention provides methods and compositions useful for separating a substance of interest from a solution, employing an adsorption support comprising hydroxyapatite or other anion exchange materials bound to a conjugate of a negatively charged peptide oligomer with a moiety capable of binding the substance of interest.

Also provided are pharmaceutical compositions for therapeutic agent delivery, endogenous substance recruitment, and bone tissue or calcified mass imaging.

The negatively charged peptide oligomers employed in the invention have an affinity for calcified tissue, particularly the hydroxyapatite component of bone tissue, thereby acting as bone targeting carriers for therapeutic agents with which they are conjugated.

In one aspect of the invention the therapeutic agents are delivered to cell surface receptors associated with bone tissue.

The peptide oligomer binds to bone tissue with an affinity that is dependent on the total negative charge of the oligomer, and on the ratio of total negative charge to number of amino acid residues in the oligomer. Accordingly, in one aspect, this invention provides conjugates with an affinity for the hydroxyapatite component of bone tissue or calcified mass, which affinity can be controlled by adjusting the total negative charge and size of the peptide oligomer.

In another aspect of the invention, the rate of degradation of the negatively charged peptide oligomer can be controlled by introducing at least one D-amino acid residue, so that resistance to enzyme cleavage of peptide bonds involving D-amino acids is provided.

Therapeutic agents and endogenous bone affecting agents embraced in the present invention include agents that affect the metabolism or health of bone tissue, thereby providing methods and compositions useful in the treatment or prevention of bone diseases such as, for example, osteosarcoma and osteoporosis.

DETAILED DESCRIPTION OF THE INVENTION

Abbreviations and Definitions

The one- and three-letter abbreviations used herein for the various common amino acids are as recommended in *Pure Appl. Chem.* 31, 639–645 (1972) and 40, 277–290 (1974) and comply with 37 CFR §1.822 (55 FR 18245, May 1, 1990). The abbreviations represent L-amino acids unless otherwise designated as D- or D,L-. Certain amino acids, both natural and non-natural, are achiral, e.g. glycine. All peptide sequences are presented with the N-terminal amino acid on the left and the C-terminal amino acid on the right.

The term "peptide oligomer" refers to a segment of at least about 3 amino acids, up to about 20 to about 50 amino acids, and does not include any natural proteins.

The term "negatively charged peptide oligomer" refers to a peptide oligomer of amino acid residues, wherein one or more amino acids, typically at least three amino acids, are negatively charged amino acids.

The term "negatively charged amino acid" refers to a natural or non-natural amino acid, regardless of chirality, containing, in addition to the C-terminal carboxyl group, at least one additional negatively charged group such as carboxyl, phosphate, phosphonate, sulfonate, or the like.

The term "conjugate" refers to and embraces a negatively charged peptide oligomer linked via a covalent bond to a therapeutic agent, moiety, or imaging agent, such as those described below, wherein such linkage is formed directly or indirectly via a linking agent.

Preferred Embodiments

The invention provides conjugates of negatively charged peptide oligomers with (a) therapeutic agents, (b) moieties capable of recruiting endogenous bone-affecting agents, and (c) imaging agents, useful for delivering such agents to bone tissue or calcified masses, and methods of use thereof. The negatively charged peptide oligomers bind strongly but reversibly to bone tissue and calcified masses. Both the binding affinity and the retention time can be controlled by use of the appropriate amino acids in the peptide oligomer. The term bone tissue as used herein, includes various calcified tissues such as bone and teeth; the term calcified masses includes such materials as calcium oxalate stones, and calcified implants.

One aspect of the invention provides a method of delivering a therapeutic agent to bone tissue of a mammalian subject comprising administering to the subject an effective amount of a composition comprising a conjugate of a negatively charged peptide oligomer with a therapeutic agent, and a pharmaceutically acceptable carrier. The negatively charged peptide oligomer, also referred to herein a peptide oligomer having negatively charged amino acids, has an affinity for the hydroxyapatite component of bone tissue and thereby binds to the bone tissue and brings the therapeutic agent with which it is conjugated into close contact with the bone tissue. In another aspect, the aforementioned composition may be used to deliver the therapeutic agent directly to cell surface receptors associated with bone tissue of the subject.

As described above, the negatively charged peptide oligomers can effectively deliver a therapeutic agent to bone tissue by being conjugated with the therapeutic agent. In another aspect of the invention, the peptide oligomers may be conjugated with moieties which are themselves capable of binding to, and thereby recruiting to bone tissue, endogenous bone affecting agents. Thus, one aspect of the invention provides a method of recruiting an endogenous bone affecting agent to bone tissue of a mammalian subject, comprising administering an effective amount of composition comprising a conjugate of a negatively charged peptide oligomer with a moiety capable of binding the bone affecting agent, and a pharmaceutically acceptable carrier. In a similar manner to that described above, such compositions may be used in a method of recruiting the endogenous bone affecting agent directly to cell surface receptors associated with bone tissue of a mammalian subject.

The affinity of the negatively charged peptide oligomers for bone tissue and calcified masses is also useful in imaging such tissue or mass. Accordingly, one aspect of the invention provides a method of imaging bone tissue or a calcified mass of a mammalian subject, comprising administering to said subject an effective amount of a composition comprising a conjugate of a negatively charged peptide oligomer with an imaging agent, and a pharmaceutically acceptable carrier, and detecting the presence of said imaging agent bound to said bone tissue or calcified mass. A wide variety of imaging agents known in the art may be employed, such as radionuclides, (e.g., technetium 99), various particles (e.g., gold, ferritin, magnetic particles, red blood cells), fluors, enzymes, enzyme substrates, enzyme cofactors, enzyme inhibitors, numerous moieties (particularly haptens), and chemiluminescers. Radionuclides are preferred and the preferred radionuclide is technetium-99 m. Chelating agents may be necessary to bind certain imaging agents, particularly radionuclides and certain particles, to the negatively charged peptide oligomer, and such chelating agents for purposes herein shall be considered to be part of the imaging agent conjugated to the oligomer. Suitable chelating agents are well known in the art and include, e.g., ethylenediaminetetraacetate (EDTA), diethylenetriaminepentaacetate, and the like. EDTA is a preferred chelating agent. As described in more detail below, controlling the affinity and rate of degradation of the oligomer conjugates enables one to precisely deliver the imaging agent for the desired period of time, thereby avoiding the shortcomings of procedures currently employed for such purpose.

Negatively charged peptide oligomers bound to hydroxyapatite are also useful in separating substances of interest from a solution by transferring the substance from a liquid phase to a solid phase. Another aspect of the invention, therefore, provides a method of separating a substance of interest from a solution containing the substance, comprising contacting hydroxyapatite with a conjugate of a negatively charged peptide oligomer with a moiety capable of binding the substance of interest to form an adsorption support and intimately contacting the adsorption support with the solution whereby the substance is bound to the adsorption support. The adsorption support and solution may be intimately contacted by a variety of methods including for example passing the solution through a column of the adsorption support, or by shaking the solution with the support. The bound substance is separated from the spent solution, as for example by filtration or by other gravitational means. The bound substance may then be separated from the adsorption support, as for example by contacting the substance bound to the support with an eluting agent that causes the substance to be eluted from the support, and collecting the eluate containing the substance of interest. It will be apparent to the skilled artisan that a number of suitable anion exchangers exist, in addition to hydroxyapatite, for binding to the negatively charged peptide oligomer. Therefore, the adsorption support could be formed from any suitable anion exchange material bound to a conjugate of a negatively charged peptide oligomer with a moiety capable of binding the substance of interest.

Another aspect of the invention provides compositions of matter and pharmaceutical compositions employed in the methods discussed above.

The binding affinity of the invention oligomer conjugates to bone tissue, calcified mass, or hydroxyapatite can be controlled by varying the total negative charge of the peptide oligomer and the ratio of total negative charge to number of amino acid residues in the peptide oligomer.

The negatively charged peptide oligomer binds to bone tissue, calcified mass, or hydroxyapatite with an affinity, and therefore a retention time, that increases with the total negative charge of the peptide oligomer. The total negative charge on the peptide oligomer must be sufficient to ensure that the peptide oligomer binds to the bone tissue, calcified mass, or hydroxyapatite. The total negative charge of the peptide oligomer is also dependent on the number of negatively charged amino acid residues in the oligomer. The presently preferred negatively charged peptide oligomer has between about 3 and about 20 negatively charged amino acids. As the negative charge is increased above the minimum charge needed for binding, the strength of the bond between the peptide oligomer and bone tissue, calcified tissue or hydroxyapatite increases. The minimum total negative charge of the peptide oligomer is preferably at least 6. A total negative charge of 6 is provided for example, by the hexamer of glutamic acid ($Glu_6$) or the trimer of 2-amino-5-phosphonovaleric acid.

Binding affinity of the peptide oligomer conjugate can also be controlled by varying the ratio of the total negative charge to the number of amino acid residues in the peptide oligomer. The presently preferred ratio of total negative charge to number of amino acid residues in the peptide oligomer is between about 0.5:1 to about 2:1. The specific ratio for a given oligomer will depend on the identity and charge density of the negatively charged groups, and the size of the oligomer.

One aspect of the invention provides the negatively charged peptide oligomer contain negatively charged groups selected from the group consisting of carboxyl, phosphate, phosphonate, and sulfonate. The presently preferred negatively charged groups are carboxyl and phosphonate. The charge density of the negatively charged groups varies depending upon the group selected, for example the carboxyl group has a negative charge of 1 whereas the phosphonate group has a negative charge of 2, so that the total negative charge of the peptide oligomer will depend upon the type of negatively charged groups that are present. The negatively charged groups may all be the same or a mixture of groups may be used in forming the negatively charged peptide oligomer.

A wide variety of amino acids may be employed in the negatively charged peptide oligomers, including naturally occurring amino acids such as glutamic acid and aspartic acid, and non naturally occurring amino acids such as 2-amino-5-phosphonovaleric acid, and the like. The peptide oligomer may consist of only one type of amino acid such as glutamic acid, or a combination of two or more different amino acids such as glutamic acid and aspartic acid. Presently preferred amino acids are glutamic acid and aspartic acid. One preferred peptide oligomer is glutamic acid decapeptide ($glu_{10}$). One aspect of the invention provides a negatively charged peptide oligomer wherein the negatively charged groups are carboxy groups and the peptide oligomer contains between about 6 to about 10 amino acids. Another aspect of the invention provides a negatively charged peptide oligomer wherein the negatively charged groups are phosphonate groups and the peptide oligomer contains between about 3 to about 5 amino acids.

The negatively charged peptide oligomers bind strongly but reversibly to bone tissue. By varying the total negative charge of the peptide oligomers as well as the ratio of total negative charge to number of amino acid residues in the peptide oligomer, a wide range of binding affinities of the peptide oligomer for bone tissue is provided. The binding affinity of the negatively charged peptide oligomers for bone tissue, calcified masses or hydroxyapatite is at least sufficient that a given size oligomer will bind thereto.

With respect to (a) the delivery of therapeutic agents, (b) recruitment of endogenous bone affecting agents, or (c) imaging of bone tissue or calcified masses, the rate of proteolytic degradation of the negatively charged peptide oligomer can be controlled by incorporating at least one D-amino acid. It will be apparent to the skilled artisan that the number and position of D-amino acids incorporated in the peptide oligomer will vary depending upon the agent to be delivered and the extent of resistance to proteolytic degradation desired. The presently preferred percentage of D-amino acid residues to total number of amino acid residues is between about 5% to about 100%. The N-terminal positions on the peptide oligomer are preferred for the D-amino acids.

The peptide oligomer may contain a random mixture of D and L amino acids. Alternatively, it may be preferable for the peptide oligomer to consist solely of D amino acids, or an ordered arrangement of D and L amino acids. It is preferred that a single diastereomeric conjugate be utilized in the methods and compositions of the present invention.

The conjugates of negatively charged peptide oligomers referred to above are useful for delivering a wide variety of therapeutic agents to bone tissue. Representative examples include antineoplastic agents such as methotrexate; bone formation stimulating agents such as insulin-like growth factors, bone morphogenic protein, fibrobast growth factor, and platelet derived growth factor; bone formation inhibiting agents such as glucocorticoids, and vitamin D derivatives such as 1, 25-dihydroxyvitamin D3; cathepsin K inhibitors, and agents which affect bone resorption such as macrophage colony stimulating factor, interleukins and other cytokines, bisphosphonate, calcitonin; and the like.

The negatively charged peptide oligomer may also be conjugated with a wide variety of moieties capable of binding endogenous bone affecting agents. This is particularly useful in making the delivery of such endogenous agents more effective than by relying solely upon their delivery from body fluids. Such moieties include, for example, antibodies capable of binding antigens, and portions of proteins, such as recognition sequences, that bind the agent of interest. The endogenous bone affecting agents include proteins, antigens, and the like, including endogenous therapeutic agents such as those mentioned above.

It is particularly useful when the therapeutic agent or the moiety to be conjugated with the peptide oligomer is itself a peptide, thereby allowing the conjugate to be prepared, for example, by a single solid-phase peptide synthesis. In addition, the conjugate could be prepared by genetic engineering, whereby recombinant DNA is used which encodes a conjugate of an endogenous or nonendogenous protein therapeutic agent or moiety with a negatively charged peptide oligomer. The recombinant DNA, which may be produced using known genetic engineering techniques, therefore encodes a conjugate of a protein with a terminal segment, or "tail", comprising the negatively charged peptide oligomer. Such conjugate would thus have a greater affinity for bone tissue than the protein itself. It should be noted that while the negatively charged peptide oligomers are no more than about 50 amino acids in length, the protein therapeutic agent or moiety which is conjugated with a negatively charged peptide oligomer is not limited as to the number of amino acids.

The conjugation of the negatively charged peptide oligomer to a therapeutic agent or moiety as set forth herein, can be effected by chemical conjugation procedures well known in the art, such as by creating peptide linkages, use of condensation agents, and by employing well known bifunctional cross-linking reagents. The conjugation may be direct, which includes linkages not involving any intervening group, e.g., direct peptide linkages, or indirect, wherein the linkage contains an intervening moiety, such as a protein or peptide, e.g., plasma albumin, or other spacer molecule. For example, the linkage may be via a heterobifunctional or homobifunctional cross-linker, e.g., carbodiimide, glutaraldehyde, N-succinimidyl 3-(2-pyridydithio) propionate (SPDP) and derivatives, bis-maleimide, 4-(N-maleimidomethyl) cyclohexane-1-carboxylate, and the like. Cross-linking may also be accomplished without exogenous cross-linkers by utilizing reactive groups on the molecules being conjugated. Methods for chemically cross-linking peptide molecules are generally known in the art, and a number of hetero- and homobifunctional agents are described in, e.g., U.S. Pat. Nos. 4,355,023, 4,657,853, 4,676,980, 4,925,921, and 4,970,156, and *Immuno Technology Catalogue and Handbook*, Pierce Chemical Co. (1989), each of which is incorporated herein by reference. Cleavable cross-linkers, particularly those that form cleavable disulfide bonds, may be employed to allow cleavage of the conjugate to free the therapeutic agent under physiological conditions. An example of such a cleavable cross-inker is 4-succinimidyloxycarbonyl-a-(2-pyridyldithio)-toluene. Such conjugation, including cross-linking, should be performed so as not to substantially affect the desired function of the peptide oligomer or entity conjugated thereto, including therapeutic agents, and moieties capable of binding substances of interest.

Conjugation of a negatively charged peptide oligomer to an imaging agent can be effected by well known procedures in the art, including having the negatively charged peptide oligomer complex a radionuclide directly, or by chemical conjugation of the negatively charged peptide oligomer with a coordination complex of a radionuclide and a chelating agent.

Conjugation of a negatively charged peptide oligomer can be effected by a linkage via the N-terminal or the C-terminal of the peptide oligomer, resulting in an N-linked peptide oligomer or a C-linked peptide oligomer, respectively.

Classical synthesis of invention peptide oligomers can be accomplished by suitable methods, such as exclusively solid phase techniques, partial solid-phase techniques, fragment condensation or classical solution couplings. For example, techniques of exclusively solid phase synthesis are set forth in the textbook "Solid-Phase Synthesis", Stewart & Young, Freemen & Company, San Francisco, 1969, and are exemplified by the disclosure of U.S. Pat. No. 4,105,603, issued Aug. 8, 1979. Classical solution synthesis is described in detail in "Methoden der Organischen Chemic (Houben-Weyl): Synthese von Peptiden", E. Wunsch (editor) (1974) Georg Thieme Verlag, Stuttgart West Germany. The fragment condensation method of synthesis is exemplified in U.S. Pat. No. 3,972,859, issued Aug. 3, 1976. Other available syntheses are exemplified in U.S., Pat. No. 3,842,067, issued Oct. 15, 1974 and U.S. Pat. No. 3,872,925, issued Jan. 28, 1975. The foregoing disclosures are incorporated herein by reference.

Alternatively, recombinant DNA synthesis may be employed to synthesize invention peptide oligomers containing natural amino acid residues. Recombinant techniques are well known to those skilled in the art. Representative methods are disclosed in Maniatis, et al., Molecular cloning, a Laboratory Manual, 2nd edition, Cold Springs Harbor Laboratory (1989), incorporated herein by reference. As mentioned above, recombinant DNA synthesis can be used to produce not only the negatively charged peptide oligomer, but also a conjugate of the peptide oligomer with an endogenous or nonendogenous protein therapeutic agent or moiety.

The invention conjugates of negatively charged peptide oligomers with therapeutic agents and moieties capable of binding endogenous bone affecting agents are useful for the prevention and treatment of a variety of conditions involving mammalian bone tissue. In particular, such conjugates are indicated for the prophylaxis and therapeutic treatment of mammalian bone conditions such as osteoporosis or osteosarcoma. Moreover, conjugates of negatively charged peptide oligomers with imaging agents are useful in bone imaging.

In general, such conjugates when used for therapeutic purposes will be administered in effective amounts for the desired purpose, with such effective amounts dependent on the disease. For example, for intravenous administration the amounts will range from between about 1.0 $\mu$g/kg body weight per hour of administration and 1.0 mg/kg body weight per hour of administration, preferably from about 10 to about 100 $\mu$g/kg body weight per hour of administration. For a 50 kg human female subject, the daily dose of active ingredient (conjugate) would be from about 50 $\mu$g/hour to about 50 mg/hour, preferably from about 500 $\mu$g/hour to about 5 mg/hour. Single or multiple administrations or a controlled release formulation of the compositions can be delivered in conventional pharmaceutical compositions as needed, to achieve the most effective results. The conjugates of negatively charged peptide oligomers with imaging agents would typically be administered in amounts between about .0.01 and about 1.0 mg/kg body weight, and the dosage would typically contain between about 5 and about 20 mCi of radioactivity when the peptide oligomer is conjugated with a radionuclide.

The selection of the exact dose and composition and the most appropriate delivery regimen will be influenced by, inter alia, the pharmacological properties of the selected therapeutic agent or endogenous agent, the nature and severity of the condition being treated, and the physical condition and mental acuity of the recipient.

Representative delivery regimens include oral, parenteral (including subcutaneous, intramuscular and intravenous), topical, rectal, buccal (including sublingual), transdermal, and intranasal. The presently preferred mode of administration is parenteral, particularly intravenous.

A further aspect of the present invention relates to pharmaceutical compositions comprising as an active ingredient a conjugate of a negatively charged peptide oligomer with (a) a therapeutic agent, (b) a moiety capable of recruiting a bone affecting agent, or (c) an imaging agent, in admixture with a pharmaceutically acceptable, non-toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in *Remington's Pharmaceutical Sciences*, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like.

Delivery of the conjugates of the present invention to a subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the invention conjugates dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189, incorporated by reference herein. The conjugates may also be formulated in cholesterol or other lipid matrix pellets, or silastomer matrix implants. Additional slow release, depot implant or injectable formulations will be apparent to the skilled artisan. See, for example, *Sustained and Controlled Release Drug Delivery Systems*, J. R. Robinson ed., Marcel Dekker, Inc., New York, 1978, and R. W. Baker, *Controlled Release of Biologically Active Agents*, John Wiley & Sons, New York, 1987, incorporated by reference herein.

As described above, conjugates of endogenous or non-endogenous proteins with negatively charged peptide oligomers are particularly useful inasmuch as they have a greater affinity for bone tissue than the proteins themselves. It has also been described that such conjugates may easily be produced by recombinant DNA synthesis. Accordingly, another valuable method of delivering a therapeutic protein to bone tissue of a mammalian subject comprises the in vivo production of a conjugate of such protein with a negatively charged peptide oligomer. Such in vivo production can be accomplished by gene therapy techniques known in the art whereby a gene encoding such conjugate is inserted into the subject and expressed.

The following specific Examples are intended to illustrate the invention and should not be construed as limiting the scope of the claims. Glutamic acid decapeptide ($Glu_{10}$) and hexapeptide ($Glu_6$) was synthesized by standard solid phase peptide synthesis. D,L-2-amino-5-phosphonovaleric acid, methotrexate, chicken liver dihydofolate reductase and N-hydroxy-succinimide were obtained from Sigma Chemical Company. 1,1-carbonyldiimidazole and dicyclohexylcarbodiimde were obtained from Aldrich Chemical Company. Succinimidyl-6-(biotinamido) hexanoate was obtained from Pierce Chemical Company, and hydroxyapatite from Bio-Rad Laboratories.

EXAMPLE I

Synthesis of the Conjugate of Glutamate Decapeptide with Methotrexate

The methotrexate derivative of glutamate decapeptide ($Glu_{10}$) was synthesized via an N-hydroxysuccinimide intermediate as described in Kulkarni, et al., *Cancer Research*, 41, 2700–2706 (1981). A solution (40 μl) containing 0.05 M methotrexate, 0.05 M N-hydroxy-succinimide and 0.05 M dicyclohexylcarbodiimide in DMF was allowed to stand at room temperature from 1 hour and then at 2–4° C. overnight. The resulting solution (10 μl) was added to 5–25 nmoles of $glu_{10}$ in 30 1 μl of 0.02 M $NaHCO_3$ at pH 8.2. The reaction mixture was shaken in the dark for 4 hours and then diluted with 70 μl of water. Unreacted methotrexate and salts were removed by shaking the reaction mixture with 10 mg of hydroxyapatite overnight, removing the supernatant and washing the hydroxyapatite with water. $Glu_{10}$ and its methotrexate conjugate were eluted by shaking the hydroxyapatite with 2×50 μl of 0.02 M pyrophosphate for 30 minutes. The conjugate was purified by high performance liquid chromatography (HPLC) on a C18 column. Its identity was confirmed by laser desorption mass spectroscopy (LDMS) (calculated for $C_{70}H_{92}N_{18}O_{35}+H^+ 1745.6$; found 1745.0).

EXAMPLE II

Recruitment of Dihydrofolate Reductase to Hydroxyapatite Using the Conjugate of Glutamate Decapeptide with Methotrexate To recruit dihydrofolate reductase to hydroxyapatite, 1 nmole of methotrexate-$glu_{10}$ conjugate was adsorbed to hydroxyapatite by shaking with 1 mg of hydroxyapatite in 20 μl of 0.01 M Tris $ClO_4$ for 6 hours (or overnight) at room temperature. The supernatant was removed by centrifugation and the hydroxyapatite was washed with 100 μl of water. Dihydrofolate reductase (0.52 nmole) in 200 μl of buffer containing 0.1 M ammonium sulfate, 0.01 M potassium phosphate, at pH 6.4 and 5% glycerol was added to the hydroxyapatite and shaken for 45 minutes. The hydroxyapatite was separated from the supernatant, washed with 100 μl of water and then eluted twice with 20 μl of 0.02 M $K_4P_2O_7$. In control experiments the methotrexate-$glu_{10}$ was replaced by $glu_{10}$. The supernatant, the washes and the pyrophosphate eluate were analyzed on a 6% arylamide SDS gel using Coumassie Blue to visualize dihydrofolate reductase. In the control experiments with glu$_{10}$, more than 75% of the dihydrofolate reductase was found in the supernatant and only a small amount in the pyrophosphate eluate. In experiments involving methotrexate-glu$_{10}$ more than 75% of the dihydrofolate reductase was found in the pyrophosphate eluate and very little in the supernatant.

EXAMPLE III

Binding of D,L-2-amino-5-phosphonovaleric Acid to Hyroxyapatite

Oligomers of D,L-2-amino-5-phosphonovaleric acid were synthesized from the monomer using carbonyl diimidazole as a condensing agent as described in Ehler et al., *Biochim. Biophys. Acta*, 434, 233–234 (1976). A solution of the monomer at pH 8 (0.05–0.01 M) was added to a threefold excess of solid carbonyl diimidazole and the resulting solution was allowed to stand for 6 hours (or overnight). Products ranging from the dimer to the pentamer were identified by paper chromatography (n-PrOH:NH$_3$:H$_2$O (7:1:2)), and samples of the oligomers were eluted from the paper. HPLC of the reaction mixture on an PRC-5 column gave a series of peaks which were assigned to oligomers of known length by co-chromatography with the material eluted from paper.

To determine the shortest oligomer that binds to hydroxyapatite, 2–3 μg of the dimer, trimer, tetramer or pentamer was separately shaken with 10 mg of hydroxyapatite and any oligomer retained by the hydroxyapatite was eluted with K$_4$P$_2$O$_7$ as described above. HPLC analysis of the supernatant and K$_4$P$_2$O$_7$ eluate showed that trimers and longer oligomers of D,L-2-amino-5-phosphonovaleric acid were found only in the eluate and therefore had been bound by the hydroxyapatite. Dimers did not bind to the hydroxyapatite and were found in the supernatant fraction.

EXAMPLE IV

Recruitment of Streptavidin to Hydroxyapatite Using the Conjugate of Glutamate Decapeptide with Biotin The biotin derivative of glutamate decapeptide was synthesized by reacting 25 nmoles of the glutamate decapeptide oligomer with 190 nmoles of succinimidyl-6-(biotinamido) hexanoate in 20 μl of 0.1 M NaHCO$_3$ buffer at pH 8.4 for 45 minutes. The product was purified on a C18 column using a 0.1% TFA-acetonitrile gradient and its identity confirmed by LDMS (Calculated for C$_{66}$H$_{97}$N$_{13}$O$_{34}$S+Na$^+$1670.6; found 1670.7).

To recruit streptavidin to hydroxyapatite, 1 nmole of biotin-glu$_{10}$ was first shaken with 1 mg of hydroxyapatite in 20 μl of 0.01 M Tris ClO$_4$ for 6 hours (or overnight) at room temperature. The supernatant was removed by centrifugation and the hydroxyapatite was washed with 100 μl of water. A solution of 0.1 nmole of $^{125}$I-labeled streptavidin (25,000–50,000 cpm) in 100 μl of buffer containing 1 M KCl and 0.01 M phosphate at pH 6.5 was added to the hydroxyapatite and shaken for 45 minutes. The supernatant was removed by centrifugation, and the conjugate treated hydroxyapatite washed several times with 200 μl of H$_2$O. The amounts of radioactivity found in the supernatant, wash and conjugate treated hydroxyapatite were then measured. In control experiments, biotin-glu$_{10}$ was replaced by glu$_{10}$. When a peptide bound to the hydroxyapatite was ligated to biotin about 70% of the streptavidin was recruited to the hydroxyapatite and 25–30% remained in the supernatant. In the control experiment, no more than 5% of the streptavidin was bound to the hydroxyapatite.

EXAMPLE V

Intravenous Formulation for Delivering a Therapeutic Agent to Bone Tissue

A representative solution for intravenous administration of a conjugate (for example, the conjugate of Example I) contains:

| | |
|---|---|
| Conjugate | 0.1 mg–20 mg |
| Dextrose Monohydrate | q.s. to make isotonic |
| Citric Acid Monohydrate | 1.05 mg |
| Sodium Hydroxide | 0.18 mg |
| Water for Injection | to 1.0 ml |

The citric acid monohydrate and the sodium hydroxide are dissolved in a sufficient quantity of the water for injection. The conjugate is dissolved in the resulting solution followed by the dextrose monohydrate. The remainder of the water for injection is added with stirring. The solution is filtered. The resulting intravenous solution may optionally be sealed in an ampoule or other suitable sterile storage container.

What is claimed is:

1. A method of delivering a therapeutic agent to bone tissue of a mammalian subject, comprising:
   administering to said subject an effective amount of a composition comprising a conjugate of a negatively charged peptide oligomer directly bonded to said therapeutic agent, wherein said conjugate is administered in a pharmaceutically acceptable carrier.

2. A method according to claim 1, wherein said delivery is to cell surface receptors on bone cells.

3. A method according to claim 1, wherein said peptide oligomer contains at least one D-amino acid and wherein the ratio of negative charges to amino acids of said oligomer is between 0.5:1 and 2:1.

4. A method according to claim 1, wherein the peptide oligomer has about 3 up to about 20 amino acids.

5. A method according to claim 1, wherein the peptide oligomer comprises amino acids having negatively charged groups and all the negatively charged groups on the peptide oligomer are the same.

6. A method according to claim 5, wherein the negatively charged groups are carboxyl or phosphonate groups.

7. A method according to claim 5, wherein the peptide oligomer contains about 6 up to about 10 amino acids, and wherein the negatively charged groups re carboxyl groups.

8. A method according to claim 5, wherein the peptide oligomer contains about 3 up to about 5 amino acids, and wherein the negatively charged groups are phosphonate groups.

9. A method according to claim 1, wherein said negatively charged groups are carboxyl, phosphate, phosphonate, sulfonate, or a combination thereof.

10. A method according to claim 1, wherein the peptide oligomer amino acids are glutamic acid, aspartic acid, or a combination thereof.

11. A method according to claim 1, wherein the therapeutic agent is an antineoplastic agent, a bone formation stimulating agent, a bone formation inhibiting agent, or an agent which affects bone resorption.

12. A method according to claim 1, wherein the therapeutic agent is a protein.

13. A method according to claim 12, wherein the conjugate is obtained by recombinant DNA expression.

14. A method according to claim 1, wherein the peptide oligomer is a glutamic acid decapetide.

15. A method according to claim 14, wherein the therapeutic agent is methotrexate.

16. A composition for delivering a therapeutic agent to bone tissue, said composition comprising a conjugate of a negatively charged peptide oligomer with said therapeutic agent, and optionally, a pharmaceutically acceptable carrier.

17. A composition according to claim 16, wherein the therapeutic agent is delivered to cell surface receptors on bone cells of a mammalian subject.

18. A pharmaceutical formulation for imaging bone tissue or a calcified mass, said formulation comprising an effective imaging amount of a conjugate of a negatively charged peptide oligomer with an imaging agent; and a pharmaceutically acceptable carrier.

19. A method of delivering a therapeutic agent to bone tissue of a mammalian subject, comprising administering to said subject an effective amount of a composition comprising a conjugate of a negatively charged peptide oligomer and said therapeutic agent, wherein said conjugate is administered in a pharmaceutically acceptable carrier, and wherein said negatively charged peptide oligomer contains at least one D-amino acid.

20. A method according to claim 19, wherein said delivery is to cell surface receptors associated with said bone tissue.

21. A method according to claim 19, wherein the ratio of negative charges to amino acids of said oligomer is 0.5:1 to 2:1.

22. A method according to claim 19, wherein said negatively charged peptide oligomer has about 3 up to about 20 amino acids.

23. A method of delivering a therapeutic agent to bone tissue of a mammalian subject comprising administering to said subject an effective amount of a composition comprising a conjugate of a negatively charged peptide oligomer and said therapeutic agent, wherein said conjugate is administered in a pharmaceutically acceptable carrier, and wherein said negatively charged peptide oligomer has about 3 up to about 20 amino acids.

24. A method according to claim 23, wherein said negatively charged peptide oligomer is directly bonded to said therapeutic agent.

25. A method according to claim 24, wherein said delivery is to cell surface receptors associated with said bone tissue.

26. A method according to claim 24, wherein said peptide oligomer contains at least one D-amino acid.

27. A method according to claim 23, wherein the ratio of negative charges to amino acids of said oligomer is 0.5:1 to 2:1.

28. A method according to claim 23, wherein said peptide oligomer contains about 6 up to about 10 amino acids.

29. A method according to claim 23, wherein said peptide oligomer contains about 3 up to about 5 amino acids.

* * * * *

UNITED STATES PATENT AND TRADEMARK OFFICE
CERTIFICATE OF CORRECTION

PATENT NO. : 6,455,495 B1
DATED : September 24, 2002
INVENTOR(S) : Orgel et al.

It is certified that error appears in the above-identified patent and that said Letters Patent is hereby corrected as shown below:

Column 12,
Line 51, delete "re" and substitute therefor -- are --;
Line 63, after "formation" delete "stimulating";

Column 13,
Line 4, change the spelling of "decapetide" to -- decapeptide --;

Column 14,
Line 18, delete "24" and substitute therefor -- 23 --; and
Line 20, delete "24" and substitute therefor -- 23 --.

Signed and Sealed this

Twenty-second Day of April, 2003

JAMES E. ROGAN
*Director of the United States Patent and Trademark Office*